United States Patent [19]

Suzuki et al.

[11] Patent Number: 4,985,558
[45] Date of Patent: Jan. 15, 1991

[54] 1,4-DIHYDROPYRIDINE DERIVATIVE

[75] Inventors: Kenichi Suzuki, Kounosu; Haruaki Inada, Omiya; Akira Kiue, Iwatsuki; Tetsuro Sano, Urawa, all of Japan

[73] Assignee: Nikken Chemicals Co., Ltd., Tokyo, Japan

[21] Appl. No.: 384,796

[22] Filed: Jul. 25, 1989

[30] Foreign Application Priority Data

Jul. 28, 1988 [JP] Japan ................... 63-186711
Mar. 14, 1989 [JP] Japan ................... 1-59828

[51] Int. Cl.$^5$ .......................................... C07D 401/04
[52] U.S. Cl. .................................................. 546/256
[58] Field of Search ......................... 546/256; 514/333

[56]  References Cited

U.S. PATENT DOCUMENTS 4,293,700 10/1981 Uldrikis et al. .................. 546/321
4,495,356  1/1985 Inoue et al. ..................... 546/268
4,690,935  9/1987 Taylor et al. .................... 514/356

FOREIGN PATENT DOCUMENTS 0123850  7/1984 European Pat. Off. .
 118120  9/1984 European Pat. Off. .
 0173204  5/1986 European Pat. Off. .
 0221382  5/1987 European Pat. Off. .
 0270926  6/1988 European Pat. Off. .
 2218644 10/1973 Fed. Rep. of Germany .
 64-31780  2/1989 Japan .
 64-31781  2/1989 Japan .

OTHER PUBLICATIONS

Nogae et al. Biochemical Pharmacology, vol. 38, No. 3, p. 519–527, 1989.
Thernber Chemical Society Reviews, vol. 8, No. 4, 1979.
Chemical Abstracts, vol. 104, No. 15, Apr. 14, 1986, p. 704.

Primary Examiner—Jane T. Fan
Attorney, Agent, or Firm—Finnegan, Henderson, Farabow, Garrett & Dunner

[57] ABSTRACT

A 1,4-dihydropyridine derivative having the formula (I):

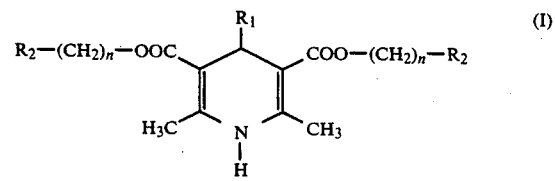

wherein $R_1$ represents 2-(5,6-dihydro-p-dioxinyl) group, $R_2$ represents a pyridyl group which may be substituted with one methyl group or ethyl group, and n is an integer of 1 to 4.

6 Claims, No Drawings

1,4-DIHYDROPYRIDINE DERIVATIVE

BACKGROUND OF THE INVENTION

1. Field of the Invention

The present invention relates to a novel 1,4-dihydropyridine derivative having an excellent pharmacological activity, more particularly it relates to a 1,4-dihydropyridine derivative useful in the therapy for tumors.

2. Description of the Related Art

Many 1,4-dihydropyridine derivatives are already known, and among these 1,4-dihydropyridine derivatives, a large number of compounds are known to have pharmacological activities. Most thereof, however, have pharmacological activities with regard to circulatory systems, and there are few reports of other pharmacological activities having an antiinflammatory effect or liver protection effect.

Concerning 1,4-dihydropyridine derivatives having some pharmacological activity with regard to tumors, U.S. Pat. No. 4,293,700 (Japanese Unexamined Patent Publication (Kokai) No. 55-500577) discloses that a 1,4-dihydropyridine compound having no substituents at the 4-position has a metastasis inhibitory effect on some tumors. Also, U.S. Pat. No. 4,690,935 (Japanese Unexamined Patent Publication (Kokai) No. 60-6613) discloses antitumor and anti-tumor metastasis agents comprising 1,4-dihydropyridine, such as nifedipine or nimodipine, as the active ingredient. Also, European Published Patent Application No. 221382 (Japanese Unexamined Patent Publication (Kokai) No. 62-87516) disclosed a method of treating malignant tumors by using a combination of a platinum coordination compound and a compound such as nifedipine or nimodipine, and European Published Patent Application No. 0270926 (Japanese Unexamined Patent Publication (Kokai) No. 63-135381) disclosed that compounds having condensed heterocyles with a special structure bonded to the 4-position of 1,4-dihydropyridine potentiate a sensitivity of multi-drug resistant tumor cells. Further, Japanese Unexamined Patent Publication (Kokai) Nos. 64-31780 and 64-31781 disclose that the compounds represented by the below-mentioned formula (I), wherein $R_2$ is replaced by an alkyloxy group and n is an integer of 2 to 4, remarkably increase the sensitivity of tumor cells having an acquired resistance.

Nevertheless, the inventions disclosed in the above U.S. Pat. No. 4,690,935 (Japanese Unexamined Patent Publication (Kokai) No. 60-6613) and European Published Patent Application No. 221382 (Japanese Unexamined Patent Publication (Kokai) No. 62-87516) use calcium channel blockers as antitumor drugs or use platinum coordination compounds which are a combination of antitumor drugs, and have a drawback in that the side effects thereof sometimes limit their practical use. More specifically, the calcium channel blockers used in the above prior arts all have a potent hypotensive action (blood pressure lowering action), and are drugs capable of revealing actions for the cardio-vascular system, even in small amount, and therefore, have a drawback in that the effect of inconvenient actions on the cardio-vascular system, such as a remarkable hypotension, cannot be avoided when such a drug is used in a large amount to the extent at which the antitumor action is exhibited. On the other hand, concerning the compound disclosed in European Published Patent Application No. 0270926 (Japanese Unexamined Patent Publication (Kokai) No. 63-135381), when administered intraperitoneally to mice, it was found that 3 of 5 mice died at 288 mg/kg (CANCER RESEARCH 49. 1722–1726, April 1, 1989), and thus it must be regarded as strongly toxic in view of the dose ($25\times2$–$75\times2$ mg/kg/day). Further, many of the compounds disclosed in Japanese Unexamined Patent Publication (Kokai) Nos. 64-31780 and 64-31781 have a calcium channel blocking action and hypotensive action, and are not always satisfactory when combined with antitumor drugs.

The present inventors have carried out intensive research into the effect of a combined use of antitumor drugs and the hypotensive action of 1,4-dihydropyridine derivatives, and found that some compounds remarkably increase the sensitivity of tumor cells to antitumor drugs, particularly tumor cells having an acquired resistance, and yet cause little hypotension as a side effect and have a low acute toxicity.

SUMMARY OF THE INVENTION

Accordingly, the main object of the present invention is to provide a 1,4-dihydropyridine derivative able to remarkably increase the sensitivity of tumor cells to antitumor drugs, particularly tumor cells having an acquired resistance, but causing little hypotension as a side effect and having a low acute toxicity.

Another object of the present invention is to provide 1,4-dihydropyridine which is useful in the therapy for tumors.

Still another object of the present invention is to provide a novel 1,4-dihydropyridine derivative.

Other objects and advantages will become apparent from the following description.

In accordance with the present invention, there is provided a 1,4-dihydropyridine derivative having the formula (I):

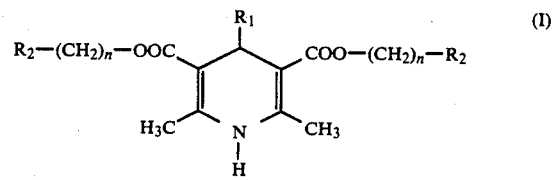

wherein $R_1$ represents 2-(5,6-dihydro-p-dioxinyl) group

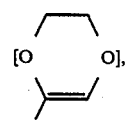

2-(5,6-dihydro-1,4-dithiinyl) group

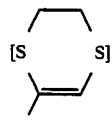

or 2-(3-methyl-5,6-dihydro-1,4-dithiinyl) group

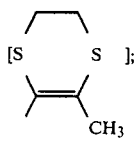

when R₁ represents 2-(5,6-dihydro-p-dioxinyl) group, R$_2$ represents a pyridyl group which may be substituted with one methyl group or ethyl group and n is an integer of 1 to 4; when R$_1$ represents 2-(5,6-dihydro-1,4-dithiinyl) group or 2-(3-methyl-5,6-dihydro-1,4-dithiinyl) group, R$_2$ represents a pyridyl group, and n represents an integer of 1 or 2.

DESCRIPTION OF THE PREFERRED EMBODIMENTS

In the present invention, among the 1,4-dihydropyridine derivatives represented by the above formula (I), one having a particularly conspicuous drug sensitivity potentiating action may be a compound wherein R$_1$ is 2-(5,6-dihydro-p-dioxinyl) group, R$_2$ is a pyridyl group or a pyridyl group substituted with one methyl group or ethyl group, and n is an integer of 1 to 3, or a compound wherein R$_1$ is 2-(5,6-dihydro-1,4-dithiinyl) group or 2-(3-methyl-5,6-dihydro-1,4-dithiinyl) group, R$_2$ is a pyridyl group, and n is 1.

Among the above, specific examples of the most preferable compounds include:

Bis[2-(6-methylpyridyl)methyl]4-(2-(5,6-dihydro-p-dioxinyl)]-2,6-dimethyl-1,4-dihydropyridine-3,5-dicarboxylate (Compound of Example 2);

Bis[3-(3-pyridyl)propyl]4-[2-(5,6-dihydro-p-dioxinyl)]-2,6-dimethyl-1,4-dihydropyridine-3,5-dicarboxylate (Compound of Example 3);

Bis[2-(5-ethylpyridyl)methyl]4-[2-(5,6-dihydro-p-dioxinyl)]-2,6-dimethyl-1,4-dihydropyridine-3,5-dicarboxylate (Compound of Example 5); and, Bis(4-pyridylmethyl) 4-[2-(3-methyl-5,6-dihydro-1,4-dithiinyl)]-2,6-dimethyl-1,4-dihydropyridine-3,5-dicarboxylate (Compound of Example 8).

These compounds having specific substituents have conspicuous drug sensitivity potentiating actions when compared with other compounds, as described hereinafter in test examples, but cause little, if any, hypotension as a side effect, and therefore, are particularly useful compounds as pharmaceuticals.

All of the 1,4-dihydropyridine derivatives represented by the above formula (I) can be prepared by utilizing reactions well known in the art and utilized for the preparation of 1,4-dihydropyridines. For example, they can be prepared by allowing 2-formyl-p-dioxene, 2-formyl-1,4-dithiene or 2-formyl-3-methyl-1,4-dithiene to react with β-aminocrotonic ester and acetoacetic ester in the presence or absence of an organic solvent by heating or by heating under reflux (method A), or by allowing 2-formyl-p-dioxene, 2-formyl-1,4-dithiene or 2-formyl-3-methyl-1,4-dithiene to react with acetoacetic ester and ammonia water in the presence or absence of an organic solvent by heating, preferably under reflux (method B).

The reactions used in these preparation methods are basically the same as the reactions used in the prior art for the preparation of 1,4-dihydropyridine compounds (e.g., the reactions used in the methods described in Japanese Patent Publication (Kokoku) Nos. 46-40625, 56-37225, and Japanese Unexamined Patent Publication (Kokai) No. 60-214786). Accordingly, the 1,4-dihydropyridine derivatives of the present invention can be also prepared by utilizing other known reactions in addition to the above methods.

The starting compounds to be used in the above preparation methods are all known compounds, and are readily available or can be easily prepared by those skilled in the art. Namely, acetoacetic ester and β-aminoctoronic ester are both compounds conventionally used as starting materials for the preparation of 1,4-dihydropyridine compounds, and are commercially readily available, or can be readily synthesized. Further, 2-formyl-p-dioxene can be prepared by the method described in M. S. Shostakovskii; Izvest. Akad. Nauk. S. S. S. R. Otdel. Khim. Nauk., 1685, (1961). 2-formyl-1,4-dithiene or 2-formyl-3-methyl-1,4-dithiene can be prepared by using 1,4-dithiene or 2-methyl1,4-dithiene as the starting material and reacting dimethylformamide and phosphorus oxychloride therewith, followed by a hydrolysis of the obtained product; specifically, they can be prepared by the method described in Japanese Unexamined Patent Publication (Kokai) No. 64-31781.

According to the present invention, the reaction product formed according to the above method, i.e., the 1,4-dihydropyridine derivative represented by the formula (I), can be separated from the reaction mixture and purified in a conventional manner, for example, by extraction with a solvent by chromatography or by crystallization.

EXAMPLES

Synthesis examples of 1,4-dihydropyridine derivatives according to the present invention and the results of pharmacological tests conducted to confirm the usefulness thereof are described, but the scope of the present invention is not limited in any way by these Examples.

Example 1

Synthesis of bis(2-pyridylmethyl) 4-[2-(5,6-dihydro-p-dioxinyl)]-2,6-dimethyl-1,4-dihydropyridine-3,5-dicarboxylate A 4.06 g (0.040 mole) amount of 2-formyl-p-dioxene, 16.4 g (0.085 mole) of 2-pyridylmethyl acetoacetate and 6.6 ml of 28% ammonia water were dissolved in 40 ml of isopropyl alcohol and heated under reflux for 20 hours. After cooling, the reaction mixture was concentrated, the residue was dissolved in ethyl acetate, and the impurities were removed by extraction with a small amount of water. The ethyl acetate layer was dried over anhydrous sodium sulfate, the solvent was evaporated, and the residue was crystallized with a solvent mixture of ethyl alcohol and n-hexane to give 6.4 g of crystals. Subsequently, recrystallization from isopropyl alcohol gave 5.48 g (yield 29.3%) of the title substance as white crystals. This substance had the following analytical values.

m.p: 157.5°–160.0° C.

IR: $\nu_{max}^{KBr}$ cm$^{-1}$: 3300(NH), 1680(C=O), 1200(C—O)

NMR(CDCl$_3$, TMS, PPM). 2.30 (6H,$_s$, 2,6-position CH$_3$); 3.90(4H,s dioxene ring OCH$_2$CH$_2$O) 4.68(1H,s, 4-position H); 5.31(4H,s, 2 ×COOCH$_2$); 5.85(1H,s, vinyl H); 6.30(1H,b,NH); 7.0–7.8, 8.4–8.7(10H,m, 2 ×pyridine ring).

Elemental analysis (C$_{25}$H$_{25}$N$_3$O$_6$): Calculated: C,64.79:H,5.44:N,9.07. Found: C,64.66:H,5.62:N,8.86.

Example 2

Synthesis of bis[2-(6-methylpyridyl)methyl]4-[2-(5,6-dihydro-p-dioxinyl]-2,6-dimethyl-1,4-dihydropyridine-3,5-dicarboxylate A 4.00 g (0.035 mole) amount of 2-formyl-p-dioxene, 16.8 g (0.081 mole) of 2-(6-methylpyridyl)methyl acetoacetate and 15 ml of 28% ammonia water were dissolved in 25 ml of isopropyl alcohol and heated under reflux for 20 hours. After cooling, the reaction mixture was concentrated, the residue was dissolved in ethyl acetate, and the impurities were removed by extraction with a small amount of water. The ethyl acetate layer was dried over anhydrous sodium sulfate, the solvent was evaporated, and the residue was subjected to silica gel column chromatography with ethyl acetate solvent. The crystals obtained were recrystallized from isopropyl alcohol to give 1.70 g (yield 10.0%) of the title substance as white crystals. This substance had the following analytical values.

m. p.: 158.0°–160.0° C.
IR:$\nu_{max}^{KBr}$cm$^{-1}$: 3270(NH), 1690(C=O), 1260(C—O)
NMR(CDCl$_3$, TMS,PPM) 2.33(6H,s,2,6-position CH$_3$); 2.53(6H,s,2 ×pyridine ring 6-position CH$_3$); 3.81(4H,s, dioxene ring OCH$_2$CH$_2$O); 4.64(1H,s, 4-position H); 5.23 (4H,ABQ,2×COOC$\underline{H_2}$); 5.83(1H,s,vinyl H); 5.86(1H,b,NH); 7.02(2H,d,2 ×pyridine ring 5-position H); 7.08(2H,d,2 ×pyridine ring 3-position H); 7.45(2H,t,2 ×pyridine ring 4-position H).

Example 3

Synthesis of bis[3-(3-pyridyl)propyl]4-[2-(5,6-dihydro-p-dioxinyl)]-2,6-dimethyl-1,4-dihydropyridine-3,5-dicarboxylate A 4.00 g (0.035 mole) amount of 2-formyl-p-dioxene, 17.9 g (0.081 mole) of 3-(3-pyridyl)propyl acetoacetate and 15 ml of 28% ammonia water were dissolved in 25 ml of isopropyl alcohol and heated under reflux for 20 hours.

After cooling, the reaction mixture was concentrated, the residue was dissolved in ethyl acetate, and the impurities were removed by extraction with a small amount of water. The ethyl acetate layer was dried over anhydrous sodium sulfate, the solvent was evaporated, and the residue was subjected to silica gel column chromatography with a solvent mixture of chloroform and methanol. The crystals obtained were washed with ether to give 2.40 g (yield 13.2%) of the title substance as pale yellow crystals. This substance had the following analytical values.

m.p. 113.5°–115.0° C.
IR:$\nu_{max}^{KBr}$cm$^{-1}$: 3250(NH), 1680(C=O), 1260(C—O)
NMR(CDCl$_3$, TMS,PPM): 1.79–2.18(4H,m,2 ×COOCH$_2$C$\underline{H_2}$CH$_2$); 2.32(6H,s,2,6-position CH$_3$) 2.74(4H,t,2 ×COOCH$_2$CH$_2$C$\underline{H_2}$); 3.92(4H,s, dioxene ring OCH$_2$CH$_2$O); 3.93–4.41(4H,m,2 ×COOC$\underline{H_2}$CH$_2$CH$_2$); 4.52(1H,s,4-position H); 5.87(1H,s,vinyl H); 5.96(1H,b,NH); 7.03–7.27(2H,m,2 ×pyridine ring 5-position H); 7.35–7.56(2H,m,2 ×pyridine ring 4-position H); 8.26–8.51(4H,m,2 ×pyridine ring 2, 6-position H).

Example 4

Synthesis of bis[2-(2-pyridyl)ethyl]4-[2-(5,6-dihydro-p-dioxinyl)]-2,6-dimethyl-1,4-dihydropyridine-3,5-dicarboxylate A 4.00 g (0.035 mole) amount of 2-formyl-p-dioxene 17.0 g (0.082 mole) of 2-(2-pyridyl)ethyl acetoacetate and 15 ml of 28% ammonia water were dissolved in 100 ml of isopropyl alcohol and heated under reflux for 48 hours. After cooling, the reaction mixture was concentrated, the residue was dissolved in ethyl acetate, and the impurities were removed by extraction with a small amount of water. The ethyl acetate layer was dried over anhydrous sodium sulfate, the solvent was evaporated, and the residue was subjected to silica gel column chromatography with a solvent mixture of ethyl acetate and acetone. The crystals obtained were recrystallized from isopropyl alcohol to give 4.34 g (yield 25.2%) of the title substance as pale yellow crystals. This substance had the following analytical values.

m.p.: 130.0°–131.0° C.
IR: $\nu_{max}^{KBr}$cm$^{-1}$: 3340(NH),1690(C=O),1210(C—O)
NMR(CDCl$_3$, TMS,PPM): 2.20(6H,s,2,6-position CH$_3$); 3.13(4H,t,2 ×COOCH$_2$C$\underline{H_2}$); 3.83(4H,s,dioxene ring OCH$_2$CH$_2$O); 4.31(1H,s,4-position H); 4.31–4.69(4H,m,2 ×COOC$\underline{H_2}$CH$_2$); 5.54(1H,s,vinyl H); 5.60(1H,b,NH); 7.00–7.23(4H,m,2 ×pyridine ring 3,5-position H); 7.43–7.67(2H,m,2 ×pyridine ring 4-position H); 8.48(2H,d,2 ×pyridine ring 6-position H).

Example 5

Synthesis of bis[2-(5-ethylpyridyl)methyl]4-[2-(5,6-dihydro-p-dioxinyl)-]2,6-dimethyl-1,4-dihydropyridine-3,5-dicarboxylate A 5.00 g (0.044 mole) amount of 2-formyl-p-dioxene, 22.7 g (0.103 mole) of 2-(5-ethylpyridyl) methyl acetoacetate and 10 ml of 28% ammonia water were dissolved in 30 ml of isopropyl alcohol and heated under reflux for 20 hours. After cooling, the reaction mixture was concentrated, the residue was dissolved in ethyl acetate, and the impurities were removed by extraction with a small amount of water. The ethyl acetate layer was dried over anhydrous sodium sulfate, the solvent was evaporated, and the residue was subjected to silica gel column chromatography with a solvent mixture of n-hexane and ethyl acetate. The crystals obtained were recrystallized from isopropyl alcohol and ether to give 4.90 g (yield 22.1%) of the title substance as pale yellow crystals. This substance had the following analytical values.

m.p.: 124.0°–126.0° C.
IR: $\nu_{max}^{KBr}$cm$^{-1}$: 3190(NH),1690(C=O),1260(C—O)
NMR(CDCl$_3$, TMS,PPM): 1.23(6H,t,2 ×CH$_2$C$\underline{H_3}$); 2.31(6H,s,2,6-position CH$_3$); 2.61(4H,q,2 ×C$\underline{H_2}$CH$_3$); 3.89(4H,s, dioxene ring OCH$_2$CH$_2$O); 4.62(1H,s,4-position H); 5.24(4H,ABq,2 ×COOC$\underline{H_2}$); 5.86(1H,s, vinyl H); 5.87(1H,b,NH); 7.29–7.51(4H,m,2 ×pyridine ring 3,4-position H); 8.32–8.35(2H,m,2 ×pyridine ring 6-position H).

Example 6

Synthesis of bis(2-pyridylmethyl) 4-[2-(5,6-dihydro-1,4-dithiinyl)]-2,6-dimethyl-1,4-dihydropyridine-3,5-dicarboxylate A 3.00 g (0.021 mole) amount of 2-formyl-1,4-dithiene, 8.20 g (0.043 mole) of 2-pyridylmethyl acetoacetate and 3.1 ml of 28% ammonia water were dissolved in 25 ml of isopropyl alcohol and heated under reflux for 20 hours. After cooling, the reaction mixture was concentrated, the residue was dissolved in ethyl acetate, and the impurities were removed by extraction with a small amount of water. The ethyl acetate layer was dried over anhydrous sodium sulfate and the solvent then concentrated. The crystals precipitated were recovered by filtration and recrystallized from ethyl alcohol to give 3.37 g (yield 33.2%) of the title substance as yellow crystals. This substance had the following analytical values.

m.p.: 161.0–162.0° C.

IR:$\nu_{max}^{KBr}$cm$^{-1}$: 3340(NH), 1700(C=0), 1260(C—O)

NMR(CDCl$_3$, TMS,PPM): 2.35(6H,s,2,6-position CH$_3$); 3.05(4H,s, dithiene ring SCH$_2$CH$_2$S); 4.93(1H,s,4-position H); 5.29(4H,ABq,2 ×COOCH$_2$); 5.93(1H,b,NH); 6.00(1H,s,vinyl H); 7.05–7.40(4H,m,2 ×pyridine ring 3,5-position H); 7.46–7.74(2H,m,2 ×pyridine ring 4 position H); 8.50(2H,d,2 ×pyridine ring 6-position H).

Example 7

Synthesis of bis(3-pyridylmethyl) 4-[2-(5,6-dihydro-1,4-dithiinyl)]-2,6-dimethyl-1,4-dihydropyridine-3,5-dicarboxylate A 4.00 g (0.027 mole) amount of 2-formyl-1,4-dithiene, 11.4 g (0.059 mole) of 3-pyridylmethyl acetoacetate and 15 ml of 28% ammonia water were dissolved in 25 ml of isopropyl alcohol and heated under reflux for 20 hours. After cooling, the reaction mixture was concentrated, the residue was dissolved in ethyl acetate, and the impurities were removed by extraction with a small amount of water. The ethyl acetate layer was dried over anhydrous sodium sulfate and the solvent then concentrated. The residue was subjected to silica gel column chromatography with a solvent mixture of chloroform and methanol, and the crystals obtained were recrystallized from isopropyl alcohol to give 2.40 g (yield 17.6%) of the title substance as yellow crystals. This substance had the following analytical values.

m.p.: 137.0°–139.0° C.

IR:$\nu_{max}^{KBr}$cm$^{-1}$: 3200(NH), 1685(C=0), 1195(C—O)

NMR (CDCl$_3$, TMS, PPM): 2.30(6H,s,2,6-position CH$_3$); 3.30(4H,s,dithiene ring SCH$_2$CH$_2$S); 4.73(1H,s,4-position H); 5.15(4H, ABq, 2 ×COOCH$_2$); 5.84(1H,s,vinyl H); 6.10(1H,b,NH); 7.10–7.29(2H,m,2 ×pyridine ring 5-position H); 7.53–7.73(2H,m,2 ×pyridine ring 4-position H); 8.32–8.70(4H,m,2 ×pyridine ring 2,6-position H).

Example 8

Synthesis of bis(4-pyridylmethyl) 4-[2-(3-methyl-5,6-dihydro-1,4-dithiinyl)]-2,6-dimethyl-1,-4-dihydropyridine-3,5-dicarboxylate A 5.00 g (0.044 mole) amount of 2-formyl-3-methyl-1,4-dithiene, 20.0 g (0.103 mole) of 4-pyridylmethyl acetoacetate and 9.5 ml of 28% ammonia water were dissolved in 30 ml of isopropyl alcohol and heated under reflux for 2 days. After cooling, the reaction mixture was concentrated, the residue was dissolved in ethyl acetate, and the impurities were removed by extraction with a small amount of water. The ethyl acetate layer was dried over anhydrous sodium sulfate and the solvent then evaporated. The residue was subjected to silica gel column chromatography with a solvent mixture of ethyl acetate and acetone, and the crystals obtained were recrystallized from ethyl acetate to give 2.32 g (yield 14.6%) of the title substance as pale yellow crystals. This substance had the following analytical values.

m.p.: 183.5°–185.5° C.

IR:$\nu_{max}^{KBr}$cm$^{-1}$: 3250(NH), 1685(C=0), 1190(C—O), 1080(C—O)

NMR (CDCl$_3$, TMS, PPM): 1.90(3H,s,dithiene ring CH$_3$): 2.30(6H,s,2, 6-position CH$_3$); 2.85–3.23(4H,m,dithiene ring SCH$_2$CH$_2$S) 5.17(4H,ABq,2 ×COOCH$_2$); 5.30(1H,s, 4-position H); 6.03(1H,b,NH); 7.07–7.23(4H,m,2 ×pyridine ring 3,5-position H); 8.45–8.57(4H,m,2 ×pyridine ring 2,6-position H).

Example 9

Synthesis of bis(4-pyridylmethyl) 4-[2-(5,6-dihydro-1,4-dithiinyl)-]2,6-dimethyl-1,4-dihydropyridine-3,5-dicarboxylate A 7.30 g (0.499 mole) amount of 2-formyl-1,4-dithiene, 21.80 g (0.113 mole) of 4-pyridylmethyl acetoacetate and 12 ml of 28% ammonia water were dissolved in 90 ml of isopropyl alcohol and heated under reflux for 48 hours. After cooling, the reaction mixture was concentrated, the residue was dissolved in ethyl acetate, and the impurities were removed by extraction with a small amount of water. The ethyl acetate layer was dried over anhydrous sodium sulfate and the solvent then concentrated. The crystals precipitated were recovered by filtration and recrystallized from. chloroform to give 4.79 g (yield 19.4%) of the title substance as pale yellow crystals. This substance had the following analytical values.

m.p.: 213.0°–215.5° C.

IR: $\nu_{max}^{KBr}$cm$^{-1}$: 1690(C=0), 1100, 1195(C—O)

NMR(CDCl$_3$, TMS, PPM): 2.35(6H,s,2,6-position CH$_3$); 3.06(4H,s,dithiene ring SCH$_2$CH$_2$S); 4.98(1H,s,4-position H); 5.20(4H,ABq,2 ×COOCH$_2$); 5.97(1H,s,vinyl H); 6.30(1H,b,NH); 7.27(4H,d,2 ×pyridine ring 3,5-position H); 8.53(4H,d,2 ×pyridine ring 2,6-position H).

Example 10

Synthesis of bis[2-(2-pyridyl)ethyl]4-[2-(5,6-dihydro-1,4-dithiinyl))-[2,6-dimethyl-1,4-dihydropyridine-3,5-dicarboxylate A 5.00 g (0.034 mole) amount of 2-formyl-1,4-dithiene, 16.0 g (0.074 mole) of 2-(2-pyridyl)ethyl acetoacetate and 17 ml of 28% ammonia water were dissolved in 50 ml of isopropyl alcohol and heated under reflux for 20 hours. After cooling, the reaction mixture was concentrated, the residue was dissolved in ethyl acetate, and the impurities were removed by extraction with a small amount of water. The ethyl acetate layer was dried over anhydrous sodium sulfate and the solvent then concentrated. The residue was subjected to silica gel column chromatography with a solvent mixture of chloroform and methanol and the crystals obtained were recrystallized from isopropyl alcohol to give 3.74 g (yield 20.9%) of the title substance as pale yellow crystals. This substance had the following analytical values.

m.p.: 131.0°–133.0° C.

IR: $\nu_{max}^{KBr}$ cm$^{-1}$: 3120(NH), 1680(C=O), 1090(C—O) NMR (CDCl$_3$, TMS, PPM): 2.21(6H,s,2,6-position CH$_3$); 2.97(4H,s,dithiene ring SCH$_2$CH$_2$S); 3.13(4H,t,2 ×COOCH$_2$CH$_2$); 4.35–4.60(4H,m,2 ×COOCH$_2$); 4.61(1H,s,4-position H); 5.67(1H,s,vinyl H); 5.75(1H,b,NH); 6.97–7.20(4H,m,2 ×pyridine ring 3,5-position H); 7.45–7.67(2H,m,2 ×pyridine ring 4-position H); 8.47(4H,m,2 ×pyridine ring 6-position H).

Example 11 (Test Example)

containing 0.1% Tween 80 and VCR was dissolved in sterilized physiological saline. The results are shown in Tables 1 to 4. In the Tables, Compound 1 is the compound obtained in Example 1, Compound 2 that obtained in Example 2, Compound 3 that obtained in Example 3, Compound 4 that obtained in Example 4, and Compound 5 that obtained in Example 5.

Antitumor agent potentiating effect $(T/V)\% =$ $$\frac{\text{Mean survival days when } VCR \text{ and the compound of the present invention are used in combination}}{\text{Mean survival days when } VCR \text{ is administered alone}} \times 100$$

TABLE 1

| Antitumor agent (μg/kg) | Compound of invention | Dose (mg/kg) | Number of animals | Survival Days (Mean ± SD) | Survival ratio T/C(%) | Potentiating effect T/V(%) |
|---|---|---|---|---|---|---|
| — | — | — | 18 | 12.0 ± 1.9 | 100 | — |
| — | Compound 1 | 100 | 6 | 12.2 ± 0.8 | 102 | — |
| VCR 30 | — | — | 12 | 12.5 ± 1.4 | 104 | 100 |
| VCR 30 | Compound 1 | 100 | 6 | 14.5 ± 1.6 | 121 | 116 |

TABLE 2

| Antitumor agent (μg/kg) | Compound of invention | Dose (mg/kg) | Number of animals | Survival Days (Mean ± SD) | Survival ratio T/C(%) | Potentiating effect T/V(%) |
|---|---|---|---|---|---|---|
| — | — | — | 12 | 9.8 ± 0.5 | 100 | — |
| — | Compound 2 | 100 | 6 | 10.3 ± 0.5 | 105 | — |
| — | Compound 3 | 100 | 6 | 10.3 ± 0.5 | 105 | — |
| VCR 30 | — | — | 12 | 10.5 ± 0.8 | 107 | 100 |
| VCR 30 | Compound 2 | 100 | 6 | 13.7 ± 1.0 | 140 | 130 |
| VCR 30 | Compound 3 | 100 | 6 | 13.7 ± 1.5 | 140 | 130 |

TABLE 3

| Antitumor agent (μg/kg) | Compound of invention | Dose (mg/kg) | Number of animals | Survival Days (Mean ± SD) | Survival ratio T/C(%) | Potentiating effect T/V(%) |
|---|---|---|---|---|---|---|
| — | — | — | 12 | 10.9 ± 1.0 | 100 | — |
| VCR 30 | — | — | 6 | 11.3 ± 1.0 | 104 | 100 |
| VCR 30 | Compound 4 | 100 | 6 | 13.7 ± 1.6 | 126 | 121 |
| VCR 30 | Compound 5 | 100 | 6 | 14.8 ± 1.2 | 136 | 131 |

TABLE 4

| Antitumor agent (μg/kg) | Positive Control Compound | Dose (mg/kg) | Number of animals | Survival Days (Mean ± SD) | Survival ratio T/C(%) | Potentiating effect T/V(%) |
|---|---|---|---|---|---|---|
| — | — | — | 15 | 10.7 ± 0.8 | 100 | — |
| VCR 30 | — | — | 12 | 11.8 ± 1.3 | 110 | 100 |
| VCR 30 | Verapamil | 30 | 6 | 14.3 ± 1.6 | 134 | 121 |
| VCR 30 | Verapamil | 60 | 6 | 15.3 ± 0.5 | 143 | 130 |

Antitumor agent potentiating effect in vincristine-resistant tumor bearing mouse One million vincristine (VCR)-resistant mouse leukemia (P388/VCR) cells were inoculated intraperitoneally into male 6 to 7-week-old CDF$_1$ mice. The compounds of this invention and VCR were administered intraperitoneally once a day for 5 consecutive days, the animals were observed, and the survival days for respective animals were determined to obtain the survival ratio (T/C) % relative to the Control. The potentiating effect of the antitumor agent (T/V) % was determined according to the formula shown below. Verapamil was employed as the positive Control compound. The compounds of this invention and the positive Control compound were suspended in a vehicle of 0.5% CMC-Na

Example 12 (Test Example)

Antitumor agent potentiating effect in vincristine-resistant tumor bearing mouse One million vincristine (VCR)-resistant mouse leukemia (P388/VCR) cells were inoculated intraperitoneally into male 6 to 7-week-old CDF$_1$ mice. The compounds of this invention and VCR were administered intraperitoneally once a day for 5 consecutive days, the animals were observed, and the survival days for respective animals were determined to obtain the survival ratio (T/C) % relative to the Control. The potentiating effect of the antitumor agent (T/V) % was determined as described above (Example 11). Nicardipine was employed as the positive Control compound, and was administered intraperitoneally for 10 days. The compounds of this invention, the positive Control compound, and vincristine were administered as described above (Example 11). The results are shown in Tables 5 to 7. In the Tables, Compound 6 is the compound obtained in Example 6, Compound 7 that obtained in Example 7, and Compound 8 that obtained in Example 8.

day the compounds of the present invention and VCR were administered once a day for 10 days; orally for the compounds of the present invention and introperitoneally for VCR. The compounds of this invention were administered orally after the treatment described above, and VCR was administered as described above. The progress thereof was observed and the survival days for respective animals were determined to obtain the survival ratio (T/C) % relative to the Control. The antitumor agent potentiating effect (T/V) % was determined as described above. The results are

TABLE 5

| Antitumor agent (μg/kg) | Compound of invention | Dose (mg/kg) | Number of animals | Survival Days (Mean ± SD) | Survival ratio T/C(%) | Potentiating effect T/V(%) |
|---|---|---|---|---|---|---|
| — | — | — | 12 | 10.3 ± 1.0 | 100 | — |
| — | Compound 6 | 100 | 5 | 10.8 ± 0.8 | 105 | — |
| — | Compound 7 | 100 | 6 | 11.0 ± 0.6 | 107 | — |
| VCR 30 | — | — | 12 | 11.4 ± 1.0 | 111 | 100 |
| VCR 30 | Compound 6 | 100 | 6 | 14.2 ± 1.2 | 138 | 125 |
| VCR 30 | Compound 7 | 100 | 6 | 13.5 ± 0.8 | 131 | 118 |

TABLE 6

| Antitumor agent (μg/kg) | Compound of invention | Dose (mg/kg) | Number of animals | Survival Days (Mean ± SD) | Survival ratio T/C(%) | Potentiating effect T/V(%) |
|---|---|---|---|---|---|---|
| — | — | — | 18 | 9.8 ± 0.9 | 100 | — |
| — | Compound 8 | 100 | 6 | 9.7 ± 1.0 | 99 | — |
| VCR 30 | — | — | 12 | 9.8 ± 0.8 | 100 | 100 |
| VCR 30 | Compound 8 | 100 | 6 | 13.5 ± 0.8 | 138 | 138 |

TABLE 7

| Antitumor agent (μg/kg) | Positive Control Compound | Dose (mg/kg) | Number of animals | Survival Days (Mean ± SD) | Survival ratio T/C(%) | Potentiating effect T/V(%) |
|---|---|---|---|---|---|---|
| — | — | — | 17 | 9.6 ± 1.2 | 100 | — |
| — | Nicardipine | 50 | 5 | 10.6 ± 1.5 | 110 | — |
| — | Nicardipine | 75 | 5 | 11.2 ± 1.1 | 117 | — |
| VCR 30 | — | — | 6 | 11.0 ± 1.8 | 115 | 100 |
| VCR 30 | Nicardipine | 50 | 6 | 12.3 ± 0.8 | 128 | 112 |
| VCR 30 | Nicardipine | 75 | 6 | 13.7 ± 1.2 | 143 | 125 |

Example 13 (Test Example)

Antitumor agent potentiatinq effect in vincristine-resistant tumor bearing mouse One million vincristine (VCR)-resistant mouse leukemia (P388/VCR) cells were inoculated intraperitoneally into male 6 to 7-week-old CDF$_1$ mice, and after one day the compounds of the present invention and VCR were administered once a day for 10 days; orally for the compounds of the present invention and introperitoneally for VCR. shown in Table 8(A). In the Table, Compound 8 is the compound obtained in Example 8.

Also, by using antitumor drug sensitive cells P388/S of mouse P388 leukemia cells, VCR was administered alone by the same method as described above, and the survival days, etc., were determined. The results are shown in Table 8(B).

TABLE 8

| Dose of VCR (μg/kg/day) | Dose of Compound 8 (mg/kg/day) | Number of animals | Survival Days (Mean ± SD) | Survival ratio T/C(%) | Potentiating effect T/V(%) |
|---|---|---|---|---|---|
| (A) | | | | | |
| — (Control) | — | 16 | 9.5 ± 0.7 | 100 | — |
| 10 | — | 10 | 9.4 ± 0.7 | 99 | 100 |
| 10 | 100 | 6 | 11.3 ± 0.8 | 119 | 120 |
| 10 | 200 | 6 | 12.3 ± 0.5 | 129 | 131 |
| 10 | 300 | 6 | 13.5 ± 0.5 | 142 | 144 |
| 30 | — | 10 | 10.3 ± 1.5 | 108 | 100 |
| 30 | 100 | 6 | 12.2 ± 1.2 | 128 | 118 |
| 30 | 200 | 6 | 14.3 ± 1.0 | 151 | 139 |
| 30 | 300 | 6 | 15.3 ± 1.5 | 161 | 149 |
| 100 | — | 9 | 10.4 ± 0.9 | 109 | 100 |
| 100 | 50 | 6 | 12.5 ± 1.6 | 132 | 120 |
| 100 | 100 | 6 | 13.5 ± 1.4 | 142 | 130 |
| 100 | 200 | 5 | 16.2 ± 2.4 | 171 | 156 |
| (B) | | | | | |
| — (Control) | — | 18 | 8.2 ± 0.5 | 100 | — |
| 10 | — | 12 | 11.8 ± 0.8 | 144 | — |

TABLE 8-continued

| Dose of VCR (μg/kg/day) | Dose of Compound 8 (mg/kg/day) | Number of animals | Survival Days (Mean ± SD) | Survival ratio T/C(%) | Potentiating effect T/V(%) |
|---|---|---|---|---|---|
| 30 | — | 11 | 13.3 ± 0.9 | 162 | — |
| 100 | — | 12 | 15.2 ± 0.8 | 185 | — |

Example 14 (Test Example)

Inhibitory effects on potassium contracture in rat rectum smooth muscle

Rat rectum (about 1.5 cm) was isolated and suspended in a Magnus tube. A Locke solution was employed as the nutrient solution, and a contraction of the intestinum rectum was caused by changing the potassium (K) concentration of this solution from 5.6 mmol (mM) to 56.0 mM. This contraction was a contraction through a membrane dependent Ca-channel mediated contraction based on depolarization by a K concentration change. The contraction was recorded by an FD-transducer and polygraph. The compounds of the present invention were permitted to act 5 minutes before changing the K concentration, and simultaneously with changing the K concentration. The compounds of the present invention and the positive Control compound were all dissolved in dimethyl sulfoxide (DMSO) and the concentrations in the nutrient solution were made $10^{-8}$ and $10^{-7}$ mole (M). A judgement was made 5 minutes after changing the K concentration, and the difference in contraction before the concentration change was indicated as an inhibition % value. Verapamil and nicardipine were employed as the positive control compound. The results are shown in Table 9. In the Table, the respective compounds have the same meanings as described in Example 11.

TABLE 9

| Compound of Invention and positive Control Compound | Inhibition ratio (%) | |
|---|---|---|
|  | $10^{-8}$ (M) | $10^{-7}$ (M) |
| Compound 1 | NT | 11.2 |
| Compound 2 | −5.6 | −2.1 |
| Compound 3 | −11.5 | −4.2 |
| Compound 4 | −6.9 | 5.2 |
| Verapamil | 13.6 | 50.2 |
| Nicardipine | 73.1 | NT |

Note
NT: Not tested

Example 15 (Test Example)

Hypotensive activity in spontaneously hypertensive rat

The systolic blood pressure was measured by using spontaneously hypertensive rats (SHR), which are a model of hypertension when examine the hypotensive activities of the compounds of the present invention and the positive Control compound. The rats were warmed for 5 minutes in a warming box at 55° C., and their blood pressure then measured by a tail cuff plethysmograph. The compounds of the present invention were administered singly and intraperitoneally at a dose of 100 mg/kg and the positive Control compound was administered singly and intraperitoneally at a dose of 10 mg/kg. The compounds of the present invention and the positive Control compound were administered in the same manner as described in Example 11. Blood pressure measurements were taken before administration and 60 minutes after administration. Nicardipine was employed as the positive Control compound. The results are shown in Table 10 and Table 11. In the Tables, the respective compounds have the same meanings as described in Example 11 and Example 12.

TABLE 10

| Compound of Invention and Positive Control Compound | Dose (mg/kg) | Systolic Blood Pressure (mmHg) | | Blood pressure change (mmHg) |
|---|---|---|---|---|
|  |  | Before administration | 60 minutes after administration |  |
| — | — | 205 | 218 | +13 |
| Compound 2 | 100 | 219 | 204 | −15 |
| Compound 5 | 100 | 221 | 187 | −34 |
| Compound 8 | 100 | 198 | 187 | −11 |
| Nicardipine | 10 | 208 | 86 | −122 |

TABLE 11

| Compound of Invention and Positive Control Compound | Dose (mg/kg) | Systolic Blood Pressure (mmHg) | | Blood pressure change (mmHg) |
|---|---|---|---|---|
|  |  | Before administration | 60 minutes after administration |  |
| — | — | 244 | 224 | −20 |
| Compound 6 | 100 | 221 | 191 | −30 |
| Compound 7 | 100 | 227 | 189 | −38 |

Example 16 (Test Example)

acute toxicity test

Male 6-week-old ICR mice were divided into groups of 2 to 5 mice per group. General signs were observed for 10 days after an intraperitoneal administration of compounds of the present invention, and the mortality rates were determined. The drugs to be tested were administered in varying amounts of 250 to 2000 mg/kg to 5 or 7 groups (a geometrical series of $\sqrt{2}$), at a dose volume of 10 ml/kg. The results are shown in Table 12. In the Table, the respective compounds have the same meanings as described above.

TABLE 12

| Compound of Invention | Dose (mg/kg) | | | | | | |
|---|---|---|---|---|---|---|---|
|  | 2000 | 1414 | 1000 | 707 | 500 | 356 | 250 |
| Compound 1 | 0/2[1] | 0/2 | 0/2 | — | 0/2 | — | 0/2 |
| Compound 2 | 0/4 | 1/5 | 0/5 | 0/5 | 0/5 | 0/5 | 0/5 |
| Compound 3 | 4/4 | 3/4 | 1/5 | 2/5 | 0/5 | 0/5 | 0/5 |
| Compound 5 | 0/2 | 0/2 | 0/3 | 0/2 | 0/3 | 0/3 | 0/3 |
| Compound 6 | 0/2 | 0/2 | 0/3 | 0/2 | 0/3 | 0/3 | 0/3 |

[1]Mortality (Dead/Treated,ip)

The 1,4-dihydropyridine derivative according to the present invention can be used in combination with an antitumor drug to potentiate the effect thereof. This effect is particularly marked for clones having acquired a resistance to the antitumor drug. For example, for a mouse transplanted with P388/VCR cells, which is a vincristine-resistant clone, substantially no life prolonging effect can be obtained by the administration of an antitumor drug alone, but a life prolonging effect can be clearly recognized upon the administration of the compound of the present invention in combination therewith (FIG. 1 to FIG. 8), and the mean survival days are clearly prolonged compared with a VCR single administration (potentiating effect 116 to 156%). This life prolonging effect is conspicuous when compared in terms of the life prolonging ratio (T/C %). For example, Compound 8 has an effect comparable to the prolonging effect when VCR is administered alone to P388/S which is a vincristine-sensitive clone (Table 8), thus completely overcoming the VCR resistance. Also, the compounds of the present invention have a very weak calcium channel blocking activity compared to many other 1,4-dihydropyridine compounds (Table 9), and very little side effects such as hypotension (Table 10 and Table 11). Further, the compounds of the present invention have an extremely low toxicity (Table 12). Therefore, the compounds of the present invention are useful for the therapy of tumors having an acquired resistance.

We claim:

1. A 1,4-dihydropyridine compound of the formula

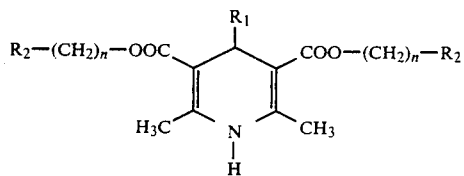

wherein $R_1$ is a 2-(5,6-dihydro-p-dioxinyl) group, $R_2$ is a pyridyl group which may be substituted with one methyl group or ethyl group, and n is an integer of 1 to 4.

2. A 1,4-dihydropyridine compound of claim 1, wherein n is an integer of 1 to 3.

3. A 1,4-dihydropyridine compound of claim 2, wherein $R_2$ is a 2-pyridyl group, a 3-pyridyl group, a 2-(6-methylpyridyl) group or a 2-(5-ethylpyridyl) group.

4. A 1,4-dihydropyridine compound of claim 2, wherein $R_2$ is a 2-(6-methylpyridyl) group and n is 1.

5. A 1,4-dihydropyridine compound of claim 2, wherein $R_2$ is a 3-pyridyl group and n is 3.

6. A 1,4-dihydropyridine compound of claim 2, wherein $R_2$ is a 2-(5-ethylpyridyl) group and n is 1.

* * * * *